(12) United States Patent
Karimov et al.

(10) Patent No.: US 11,172,932 B2
(45) Date of Patent: Nov. 16, 2021

(54) APPARATUS AND METHOD FOR ASSISTING IN HEMOSTASIS OF A VESSEL

(71) Applicant: THE CLEVELAND CLINIC FOUNDATION, Cleveland, OH (US)

(72) Inventors: Jamshid Karimov, Cleveland Heights, OH (US); Kiyotaka Fukamachi, Mayfield Heights, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 711 days.

(21) Appl. No.: 15/699,259

(22) Filed: Sep. 8, 2017

(65) Prior Publication Data

US 2018/0070949 A1      Mar. 15, 2018

Related U.S. Application Data

(60) Provisional application No. 62/393,038, filed on Sep. 11, 2016.

(51) Int. Cl.
*A61B 17/12* (2006.01)
*A61B 17/00* (2006.01)

(52) U.S. Cl.
CPC .......... *A61B 17/12009* (2013.01); *A61B 2017/00557* (2013.01); *A61B 2017/00778* (2013.01); *A61B 2017/00884* (2013.01); *A61B 2017/12004* (2013.01); *A61B 2017/12018* (2013.01)

(58) Field of Classification Search
CPC .... A61B 17/12009; A61B 2017/00557; A61B 2017/00778; A61B 2017/12004; A61B 2017/12018

See application file for complete search history.

(56) References Cited

U.S. PATENT DOCUMENTS 3,726,279 A * 4/1973 Barefoot ............... A61B 17/11
606/151
4,233,980 A   11/1980 McRae et al.
(Continued)

OTHER PUBLICATIONS

Sakakibara, Yutaka, et al. "Novel wrapping technique with Insertion of fat tissue for hemostasis in aortic surgery." The Annals of thoracic surgery 89.3 (2010): 992-993.

(Continued)

*Primary Examiner* — Diane D Yabut
*Assistant Examiner* — Christina C Lauer
(74) *Attorney, Agent, or Firm* — Tarolli, Sundheim, Covell & Tummino LLP

(57) ABSTRACT

A hemostatic vessel band is provided. The hemostatic vessel band has a membrane. A plurality of cells extend transversely from a membrane second surface. Each of the cells has a cell chamber that is defined by the membrane second surface and a plurality of cell walls. When the hemostatic vessel band is selectively fastened circumferentially about a vessel to at least partially cover the target site. The hemostatic vessel band applies radially inward pressure to at least a portion of the vessel and at least a portion of the target site. Each cell chamber that is positioned transversely adjacent to at least a portion of the target site forms one isolation zone of a plurality of isolation zones. Each isolation zone is at least partially isolated from each of the other isolation zones and from any vessel surface adjacent to the isolation zone.

28 Claims, 14 Drawing Sheets

(56) References Cited

U.S. PATENT DOCUMENTS

| | | | | |
|---|---|---|---|---|
| 4,586,501 | A | * | 5/1986 | Claracq .................. A61B 17/12 606/142 |
| 4,708,140 | A | * | 11/1987 | Baron .................... A61B 17/12 606/158 |
| 4,889,167 | A | * | 12/1989 | Morris .................. F16L 55/172 138/99 |
| 5,514,155 | A | * | 5/1996 | Daneshvar ......... A61B 17/1325 128/118.1 |
| 6,030,394 | A | | 2/2000 | Hart |
| 7,329,792 | B2 | * | 2/2008 | Buckman ................ A61F 13/00 602/42 |
| 2002/0022891 | A1 | | 2/2002 | Gerard et al. |
| 2010/0094409 | A1 | * | 4/2010 | Barker ...................... A61F 2/07 623/1.46 |

OTHER PUBLICATIONS

Sottiurai, V. S., and R. C. Batson. "Technique to prevent aortic anastomotic bleeding and kinking with bifurcated PTFE grafts." European journal of vascular surgery 5.5 (1991): 577-579.

Vander Salm, Thomas J., and Ann J. Toran. "An aortic cinch to quell suture line bleeding." The Annals of thoracic surgery 89.3 (2010): 990-991.

* cited by examiner

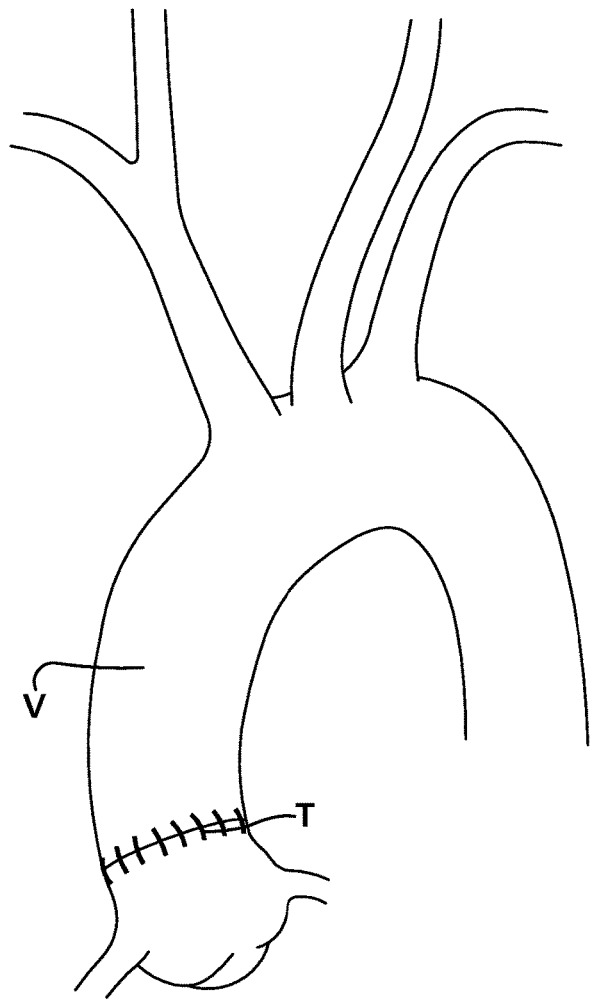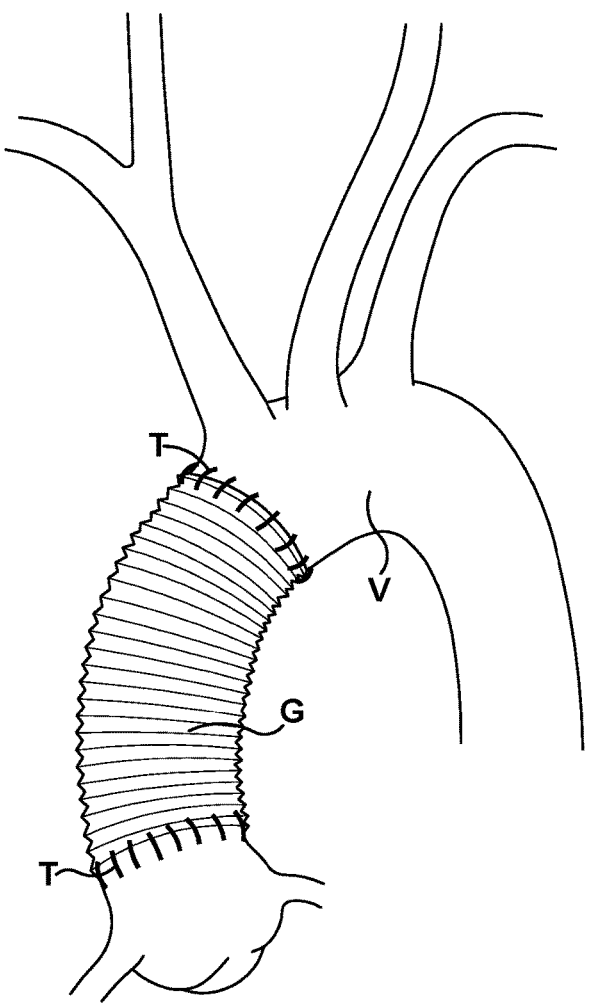
Fig. 12                    Fig. 13

APPARATUS AND METHOD FOR ASSISTING IN HEMOSTASIS OF A VESSEL

TECHNICAL FIELD

This application claims priority from U.S. Provisional Application No. 62/393,038, filed 11 Sep. 2016, the subject matter of which is incorporated herein by reference in its entirety.

TECHNICAL FIELD

This disclosure relates to an apparatus and method for use of a hemostatic vessel band and, more particularly, to an apparatus and method for assisting in hemostasis of a vessel.

BACKGROUND

Anastomosis is a surgical technique applied during procedures such as aortic valve replacements, ascending aorta replacements, aortic arch replacements, and surgical treatments for aortic dilation (thoracic and/or abdominal aneurysms). In these procedures, the aortic wall may be at least partially cut and closed using standard anastomotic techniques. Further, fabric grafts may be anastomosed to a native vessel during a total or partial replacement of a segment of the native vessel. Persistent bleeding may occur at any time during surgical procedures involving anastomosis or any invasive manipulation on the aorta or other major vessels. It may be desirable by surgeons to manage the bleeding, reinforce the bleeding site, to promote hemostasis, and/or to take some preventive measure to avoid future bleeding from potential bleeding sites.

SUMMARY

In an aspect, a hemostatic vessel band is provided. The hemostatic vessel band has a membrane. The membrane has a membrane first surface and an oppositely facing membrane second surface. A plurality of cells extends transversely from the membrane second surface. Each of the cells has a cell chamber that is defined by the membrane second surface and a plurality of cell walls. The plurality of cell walls has a vessel engaging edge for concurrently contacting at least a portion of a vessel surface and at least a portion of a target site on the vessel. When the hemostatic vessel band is selectively fastened circumferentially about a vessel to at least partially cover the target site, the hemostatic vessel band applies radially inward pressure to at least a portion of the vessel and at least a portion of the target site. Each cell chamber that is positioned transversely adjacent to at least a portion of the target site forms one isolation zone of a plurality of isolation zones. Each isolation zone is at least partially isolated from each of the other isolation zones and from any vessel surface adjacent to the isolation zone.

In an aspect, a method for assisting in the hemostasis of a vessel. A hemostatic vessel band is provided. The hemostatic vessel band has a membrane. The membrane has a membrane first surface and an oppositely facing membrane second surface. A plurality of cells extends transversely from the membrane second surface. Each of the cells has a cell chamber that is defined by the membrane second surface and a plurality of cell walls. The plurality of cell walls has a vessel engaging edge for concurrently contacting at least a portion of a vessel surface and at least a portion of a target site on the vessel. At least one target site is located on the vessel. At least a portion of the vessel is encircled with the hemostatic vessel band so that at least a portion of the cells are transversely adjacent to at least a portion of the target site. Radially inward pressure is provided from the hemostatic vessel band to the portion of the vessel that is encircled by the hemostatic vessel band. With the radially inward pressure, the portion of the cells which are transversely adjacent to at least a portion of the target site is caused to engage the target site. Isolation zones are formed with each cell chamber that is positioned transversely adjacent to at least a portion of the target site. Each isolation zone is at least partially isolated from each of the other isolation zones and from any vessel surface adjacent to the isolation zone.

BRIEF DESCRIPTION OF THE DRAWINGS

For a better understanding, reference may be made to the accompanying drawings, in which:

FIGS. 12-19 illustrate examples of the aspect of FIG. 1 in an example use environment.

DESCRIPTION OF EMBODIMENTS

Figure 1:
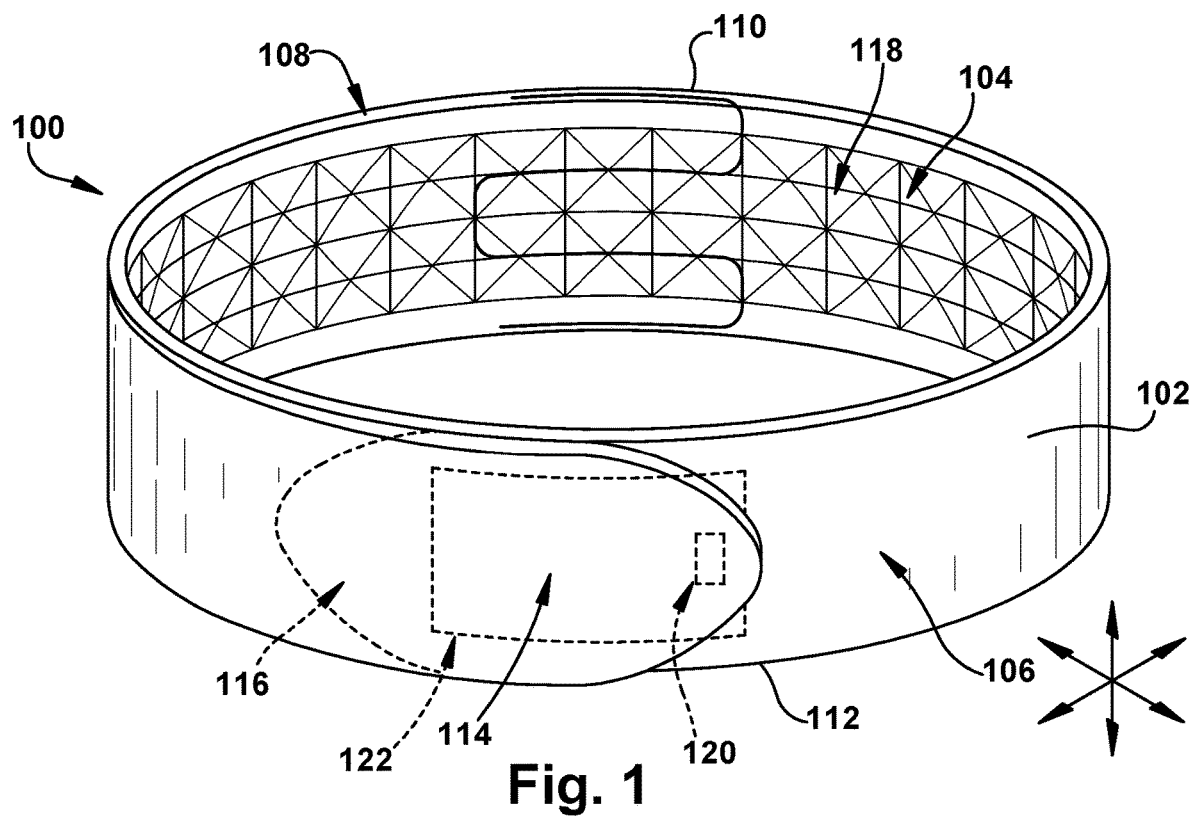
FIG. 1 is a front perspective view of a hemostatic vessel band according to one aspect of the present invention.

Unless defined otherwise, all technical and scientific terms used herein have the same meaning as is commonly understood by one of ordinary skill in the art to which the present disclosure pertains.

As used herein, the term "patient" can refer to any warm-blooded organism including, but not limited to, human beings, pigs, rats, mice, dogs, goats, sheep, horses, monkeys, apes, rabbits, cattle, farm animals, livestock, etc.

As used herein, the term "user" can be used interchangeably to refer to an individual who prepares for, assists, and/or performs a procedure.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the phrase "between X and Y" can be interpreted to include X and Y.

It will be understood that when an element is referred to as being "on," "attached" to, "connected" to, "contacting," etc., another element, it can be directly on, attached to, connected to or contacting the other element or intervening elements may also be present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such "below," "above," "over" and the like, may be used herein for ease of description to describe one element or feature's relationship to another element(s) or feature(s) as illustrated in the Figures. It will be understood that the spatially relative terms can encompass different orientations of a device in use or operation, in addition to the orientation depicted in the Figures. For example, if a device in the Figures is inverted, elements described as "below" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

The invention comprises, consists of, or consists essentially of the following features, in any combination.

FIG. 1 depicts a hemostatic vessel band 100. The hemostatic vessel band 100 may have any suitable configuration to provided desired flexibility to facilitate usage of the hemostatic vessel band 100, and desired conformation of the hemostatic vessel band 100 to the vessel surface VS, as shown and described herein. For example, the hemostatic vessel band 100 could have a durometer hardness in the range of 45-55 Shore A. The hemostatic vessel band 100 has a membrane 102 and a plurality of cells 104. The membrane 102 has a membrane first surface 106 and an oppositely facing membrane second surface 108. The membrane 102 has membrane first and second major edges 110, 112. The membrane first major edge 110 is laterally spaced, and oppositely facing, from the membrane second major edge 112. The term "lateral" is used herein to indicate a substantially vertical direction, in the orientation of FIG. 1. The membrane 102 has a membrane first end 114, a membrane second end 116, and a membrane body 118 longitudinally extending between the membrane first and second ends 114, 116. The term "longitudinal" is used herein to indicate a direction substantially perpendicular to the "lateral" direction, and is shown as the horizontal direction, in the orientation of FIG. 1.

The membrane first end 114 may have at least one first fastening element 120. At least one of the membrane first end 114, the membrane second end 116, and the membrane body 118 may have at least one second fastening element 122. The at least one first fastening element 120 may at least partially engage the at least one second fastening element 122 to selectively fasten the hemostatic vessel band 100 circumferentially about a vessel V. The vessel V may be at least one of an aorta, an artery, an arteriole, a capillary, a venule, a vein, or any other similar body lumen. When the hemostatic vessel band 100 is fastened circumferentially about the vessel V, the hemostatic vessel band 100 is considered to be in a ringed condition. In the ringed condition, the hemostatic vessel band 100 has the shape of a ring. (It should be understood that the term "ring" herein does not necessarily indicate a perfect circle, but admits of any suitable contour as is useful to desirably conform to the vessel surface VS.) The ringed hemostatic vessel band 100 is shown in FIG. 1. When the hemostatic vessel band 100 is in the ringed condition, at least a portion of the membrane first end 114 may be positioned adjacent to at least one of the membrane first end 114, the membrane second end 116, and the membrane body 118. The engagement of the first fastening element 120 to the second fastening element 120 may have various fastening conditions that may affect the diameter of the ringed hemostatic vessel band 100. The diameter of the ringed hemostatic vessel band 100 in one fastening condition may have a smaller diameter than the diameter of the encircled hemostatic vessel band 100 in another fastening condition.

Figure 2:
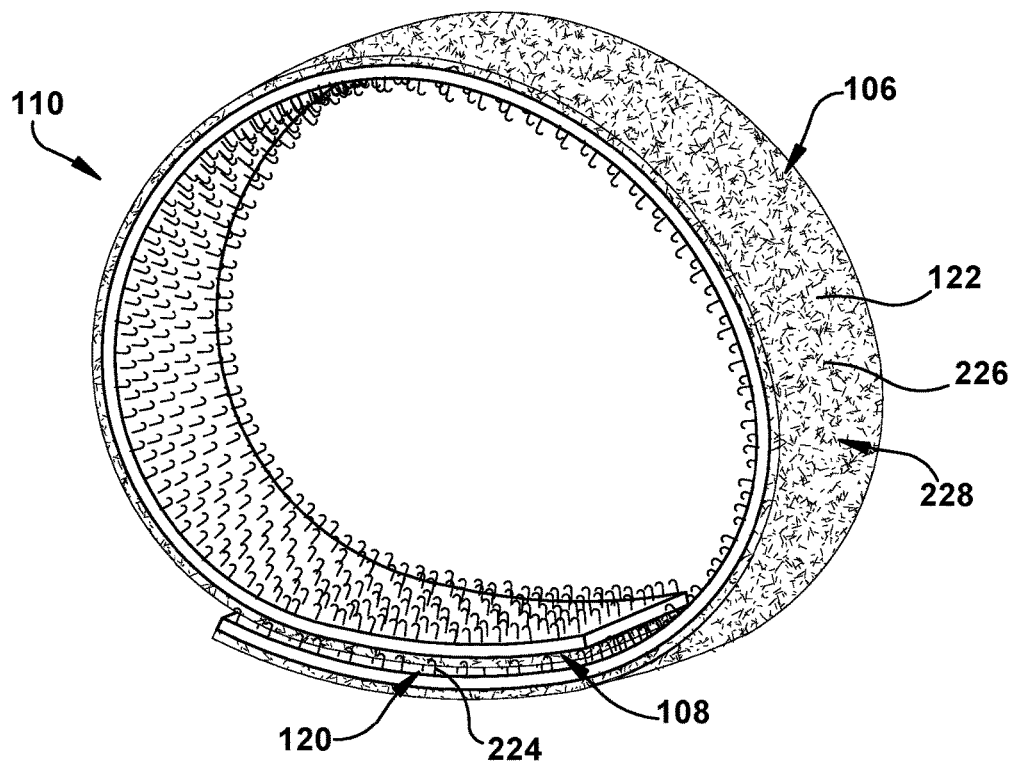
FIG. 2 is a bottom view of the aspect of FIG. 1.

As shown in FIG. 2, the first fastening element 120 may include a plurality of hooks 224 extending transversely from the membrane second surface 108. The term "transverse" is defined herein to indicate a substantially vertical direction, in the orientation of FIG. 2. The second fastening element 122 may include a plurality of loops 226. The plurality of loops 226 may form a mesh 228 that transversely extends from at least a portion of the membrane first surface 106. The mesh 228 may extend transversely from a portion, up to an entirety, of the membrane first surface 106. To fasten the hemostatic vessel band 100 about the vessel V and/or place the hemostatic vessel band 100 in the ringed condition, a portion of the membrane first end 114 having the plurality of loops 226 may selectively overlap at least one of the membrane second end 116, the membrane body 118, and another portion of the membrane first end 114 so that the plurality hooks 224 may engage the plurality of loops 226. The first and second fastening elements 120, 122 may be at least one of a hook and loop fastener, an adhesive, a magnetic fastener, a snap fastener, a hook and eye fastener, a button, a zipper, a string and eye fastener, a saw tooth fastener, or any other suitable fastener or combination of fasteners.

Figure 3:
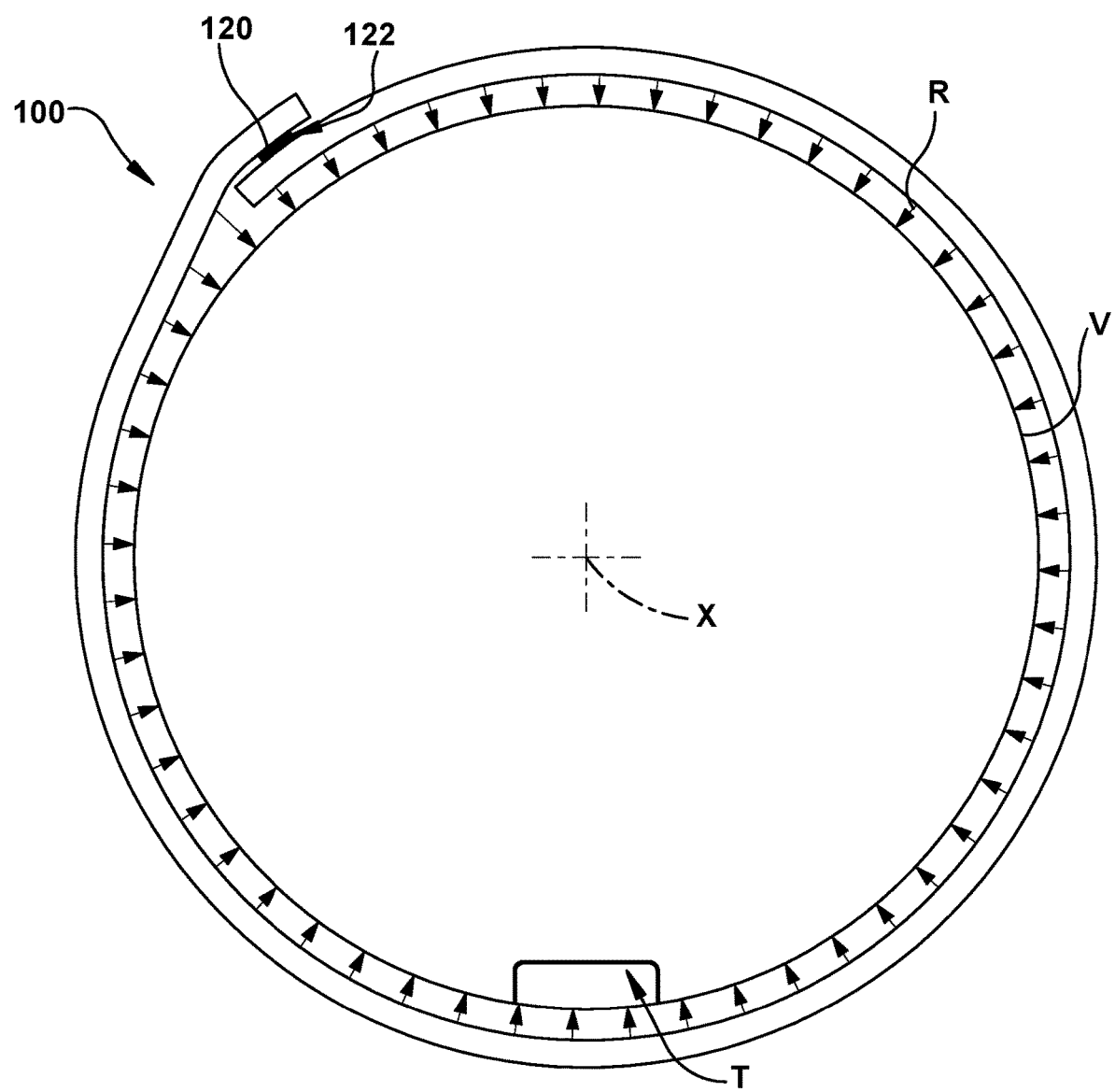
FIG. 3 is a top view of the aspect of FIG. 1.

As shown in FIG. 3, when the hemostatic vessel band 100 is selectively fastened circumferentially about a vessel V to at least partially cover a target site T on the vessel V, the hemostatic vessel band 100 may apply radially inward pressure R to at least a portion of the vessel V and at least a portion of a target site T. The term "radial" is used herein to indicate a direction substantially perpendicular to the "lateral" direction, and is shown via arrows R in FIG. 3 extending outward from a central lateral axis X, in the orientation of FIG. 3. The target site T may be at least one of a suture line, an anastomosis suture line between two portions of a vessel V, an anastomosis suture line between a vessel V and a graft G, an anastomosis suture line between a graft G and another graft G, individual points on a suture line, a cut and/or punctured portion on a vessel V, or any other portion of a vessel V that is, or could be, bleeding or oozing some fluid in an unwanted manner. The term "ooze" is defined herein as to pass or flow through or as if through small openings or interstices. The hemostatic vessel band 100 may be at least partially formed from an elastomeric material. In such case, when the hemostatic vessel band 100 is selectively fastened circumferentially about the vessel V and at least a portion of the target site T, the innate elasticity of the elastomeric material provides at least a portion of the radial inward pressure R to at least a portion of the vessel V and at least a portion of the target site T. The radial inward pressure R caused by the hemostatic vessel band 100 formed from the elastomeric material is caused by the hemostatic vessel band 100 radially compressing the vessel V. The term "compress" is herein used to indicate exerting a radially inward force.

At least a portion of the radially inward pressure R may be provided by the engagement of the first fastening element 120, when provided, to the second fastening element 122, when provided. As described above, when the first and second fastening elements 120, 122 are engaged, the hemostatic vessel band 100 may be in the ringed condition. The diameter of the ringed hemostatic band 100 may be increased and/or decreased by placing the first fastening element 120 and second fastening element 122 in various fastening conditions. The diameter of the ringed hemostatic vessel band 100 in one fastening condition may be larger than the diameter of the vessel V. The diameter of the ringed hemostatic vessel band 100 in another fastening condition may be smaller than the diameter of the vessel V. The smaller the diameter of the ringed hemostatic vessel band 100 tightly fastened circumferentially about the vessel V, the greater the radially inward pressure R provided by the hemostatic vessel band 100. This is because the hemostatic vessel band 100 may compress the vessel V when the hemostatic vessel band 100 has a diameter smaller than the diameter of the vessel V in which the hemostatic vessel band 100 encircles. Thus, a user can selectively provide a predetermined amount of radially inward pressure R by placing the ringed hemostatic vessel band 100 in a fastening condition that correlates to the predetermined amount of radially inward pressure R desired.

Figure 4:
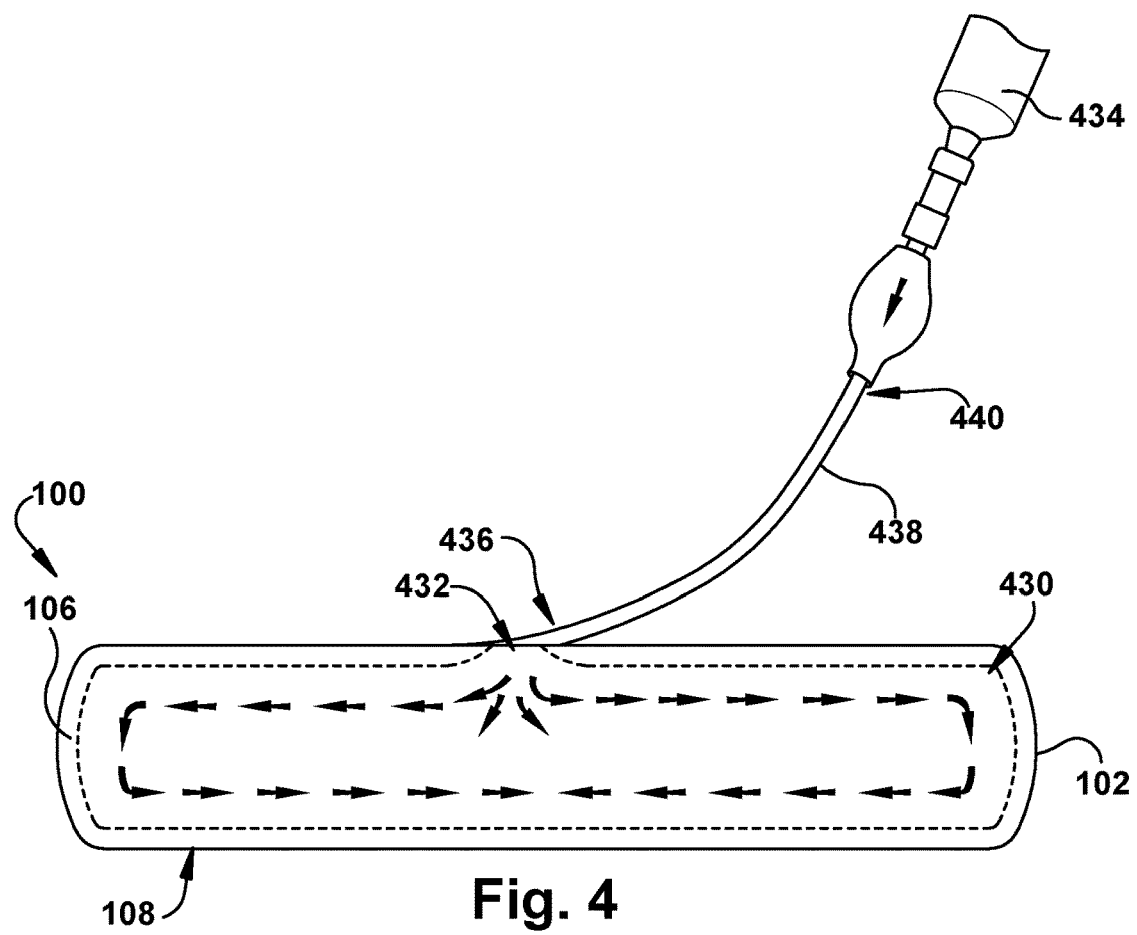
FIG. 4 is a front view of the aspect of FIG. 1.
Figure 5:
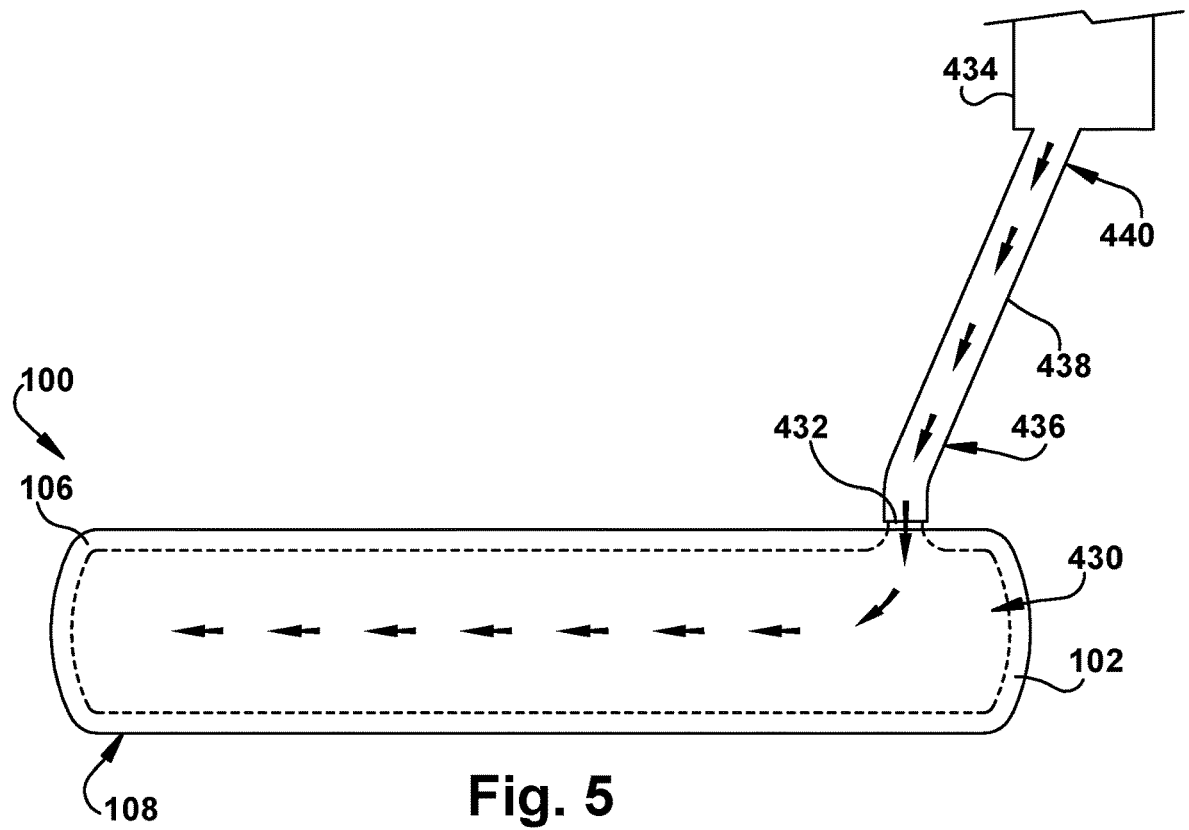
FIG. 5 is a front view of the aspect of FIG. 1.

As shown in FIGS. 4-5, the membrane may have a membrane inflatable space 430 transversely between the membrane first and second surfaces 106, 108. The membrane 102 may have an inflation valve 432. The inflation valve 432 may selectively place the inflatable membrane space 430 in fluid communication with a pressure source 434. The inflation valve 432 may be selectively engaged with a pressure line distal end 436 to place the inflation valve 432 and membrane inflatable space 430 in fluid communication with a pressure line 438. When the inflation valve 432 is engaged with the pressure line distal end 436, the pressure line proximal end 440 may be selectively engaged with the pressure source 434 to place the membrane inflatable space 430 in fluid communication with the pressure source 434. When the pressure source 434 is in fluid communication with the membrane inflatable source 430, the pressure source 434 may be actuated to selectively inflate and/or deflate the membrane inflatable space 434. After the hemostatic vessel band 100 is fastened circumferentially about the vessel V, the selective inflation of the membrane inflatable space 430 provides a predetermined portion of the radially inward pressure R to at least a portion of the vessel V and at least a portion of the target site T. In particular, the more membrane inflatable space 430 is selectively inflated, the greater the amount of radially inward pressure R that is provided to the vessel V. This is because as the membrane inflatable space 430 is increasingly inflated, the hemostatic vessel band 100 is caused to increasingly compress the vessel V.

Figure 6:
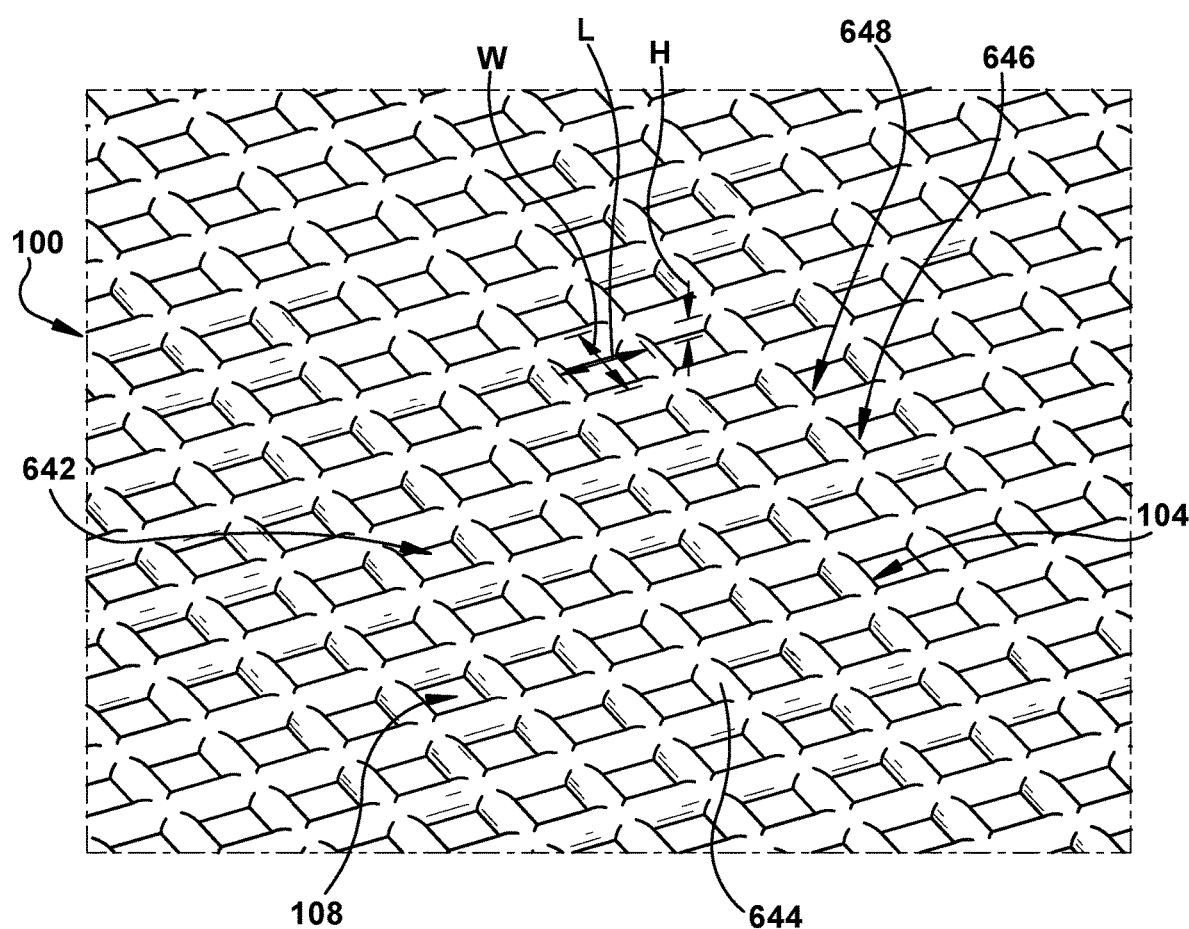
FIG. 6 is a front view of an element of the aspect of FIG. 1.

Referring back to FIG. 1, the plurality of cells 104 extends transversely from the membrane second surface 108. As shown in FIG. 6, each of the cells 104 may have a longitudinal width W of two (2) millimeters, a lateral length L of two (2) millimeters, and a transverse height H of about twenty-five hundredths (0.25) to about seventy-five hundredths (0.75) of a millimeter. Each of the cells 104 are not limited to these dimensions, and may have any desired length L, width W, and height H. Each of the cells 104 may be directly adjacent to at least one of the other cells 104. The cells 104 may be collectively evenly distributed across an entirety, or a portion of, of the membrane second surface 108. Each of the cells 104 has a cell chamber 642 that is defined by the membrane second surface 108 and a plurality of cell walls 644.

Figure 7:
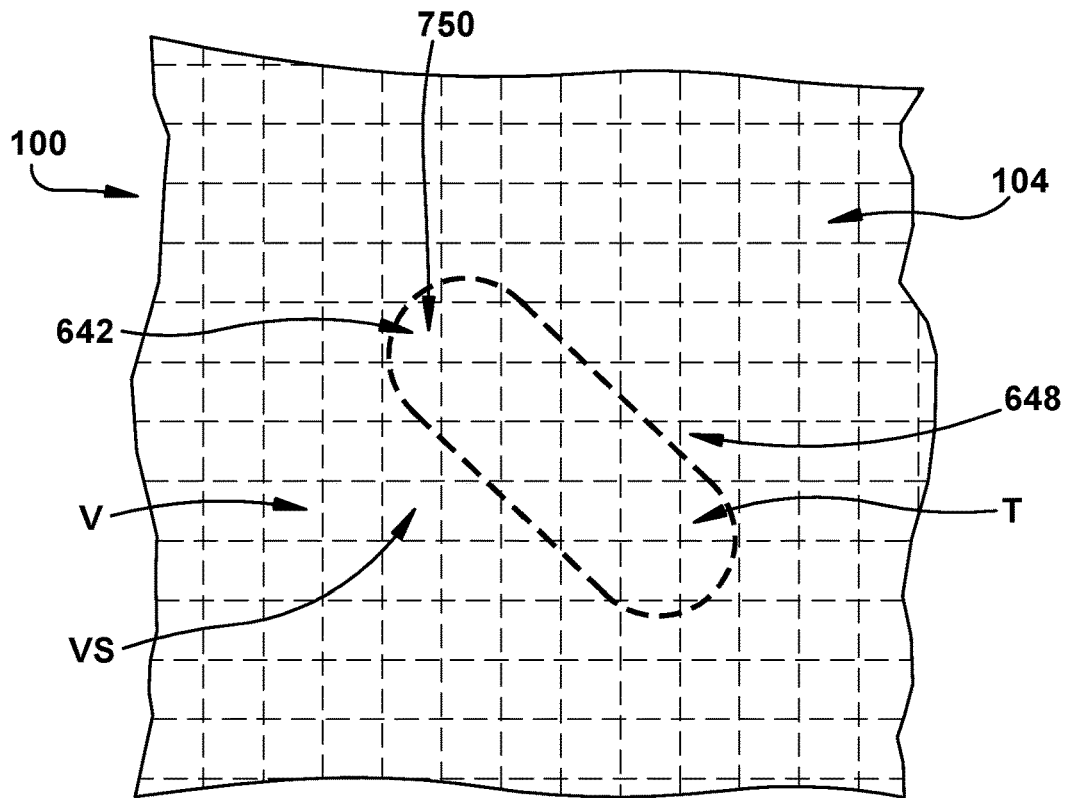
FIGS. 7-9 illustrate an example sequence of operation of a portion of the aspect of FIG. 1.

Each of the cell walls 644 has a first cell edge 646 and a vessel engaging edge 648. The first cell edge 646 is transversely spaced, and oppositely facing, from the vessel engaging edge 648. The first cell edge 644 contacts the membrane second surface 108. The first cell edge 644 may be permanently attached to, removably attached to, and/or formed integrally with the membrane second surface 108. As shown in FIG. 7, when the vessel engaging edge 648 is disposed on at least a portion of the vessel V and at least a portion of a target site T on the vessel V, the vessel engaging edge 648 concurrently contacts at least a portion of a vessel surface VS and at least a portion of the target site T on the vessel V. The vessel engaging edge 648 maintains contact between the hemostatic vessel band 100 and at least one of the vessel surface VS and the target site T to prevent the hemostatic vessel band 100 from egressing from a predetermined use position.

Figure 8:
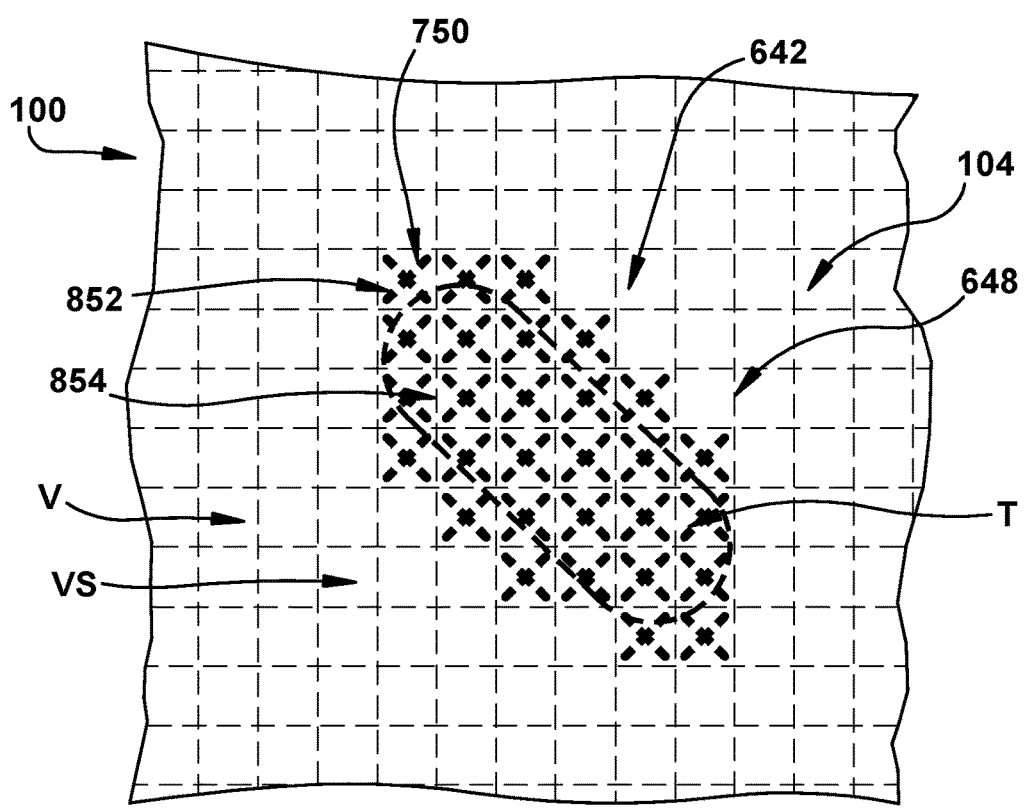
Figure 9:
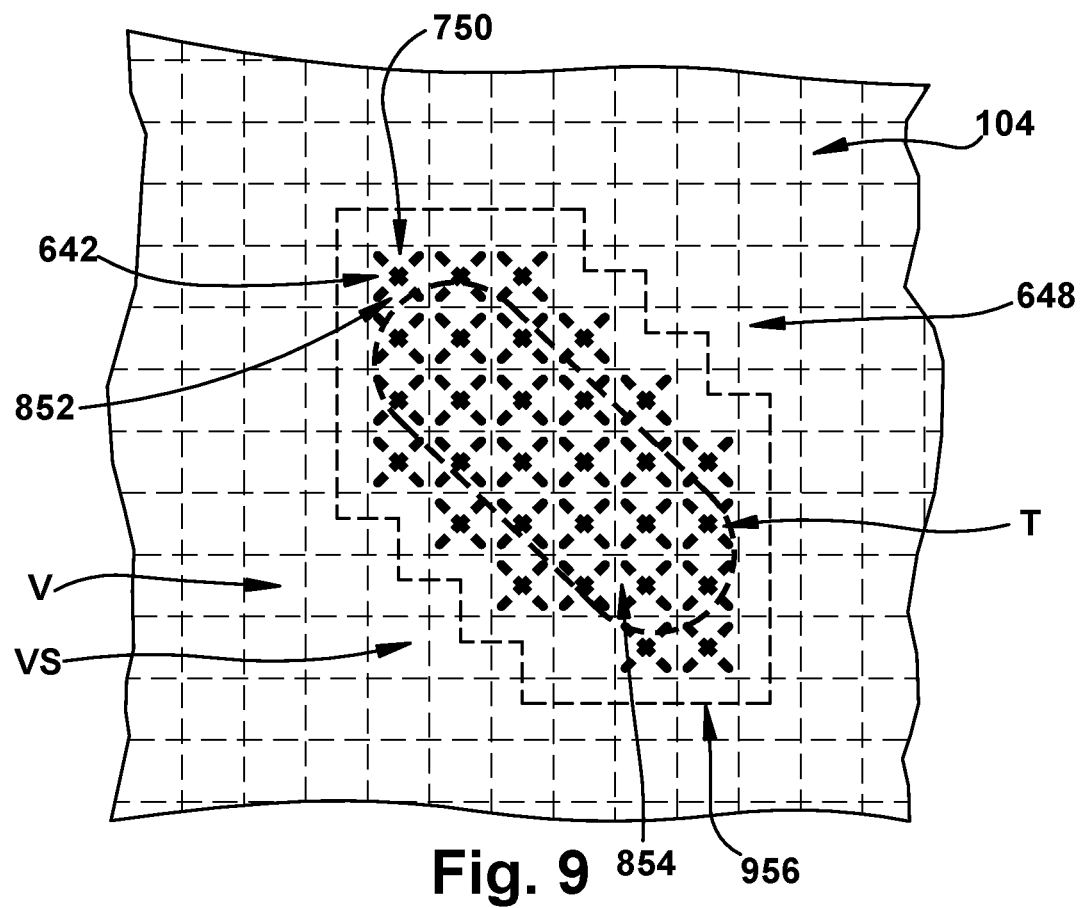

As shown in FIGS. 7-8, when the hemostatic vessel band 100 is selectively fastened circumferentially about a vessel V to at least partially cover the target site T, each cell chamber 642 that is positioned transversely adjacent to at least a portion of the target site T forms one isolation zone 750 of a plurality of isolation zones 750. At least one of the isolation zones 750 has a corresponding bleeding locale 852 at the target site T. The bleeding locale 852 may be a locale on target site T that is bleeding and/or oozing biological material. Each isolation zone 750 is at least partially isolated from each of the other isolation zones 750 and from any vessel surface VS adjacent to the isolation zone 750. The isolation is formed by the radially inward pressure R provided by the hemostatic vessel band 100 causing the vessel engaging edge 648 of the walls 644 of the cells 104 to engage and transversely extend into the vessel surface VS. The engagement of the vessel engaging edge 648 of each of the cells 104 creates a substantially effective seal 854 between each of the isolation zones 750. A substantially effective seal 854 is a seal between the isolation zones, and/or between at least one isolation zone 750 and any adjacent vessel surface VS, that provides for little to no leakage of blood and/or other biological material from one isolation zone 750 to another isolation zone 750, and/or from one isolation zone 750 to any adjacent vessel surface VS. Any slight leakage that may occur between each of the isolation zones 750, and/or between at least one isolation zone 750 and any adjacent vessel surface VS, will not significantly affect the functionality of the hemostatic vessel band 100. Because of the seal 854, the bleeding locale 850 at a corresponding isolation zone 750 is isolated from at least one of another bleeding locale 850, another isolation zone 750, and a vessel surface VS surrounding the isolation zone 750 so that blood and/or other biological materials from the bleeding locale 850 is directed into the corresponding isolation zone 750 and is substantially prevented from flowing to at least one of another bleeding locale 850, another isolation zone 750, and the vessel surface VS surrounding the isolation zone 750. As shown in FIG. 9, each of the cell chambers 642 contacting the vessel surface VS that are adjacent to the isolation zones 750 may collectively form a seal boundary 856 that surrounds the isolation zones 750 to substantially assist in the isolation of the blood and/or other biological materials from the vessel surface VS surrounding the isolation zones 750.

Figure 10:
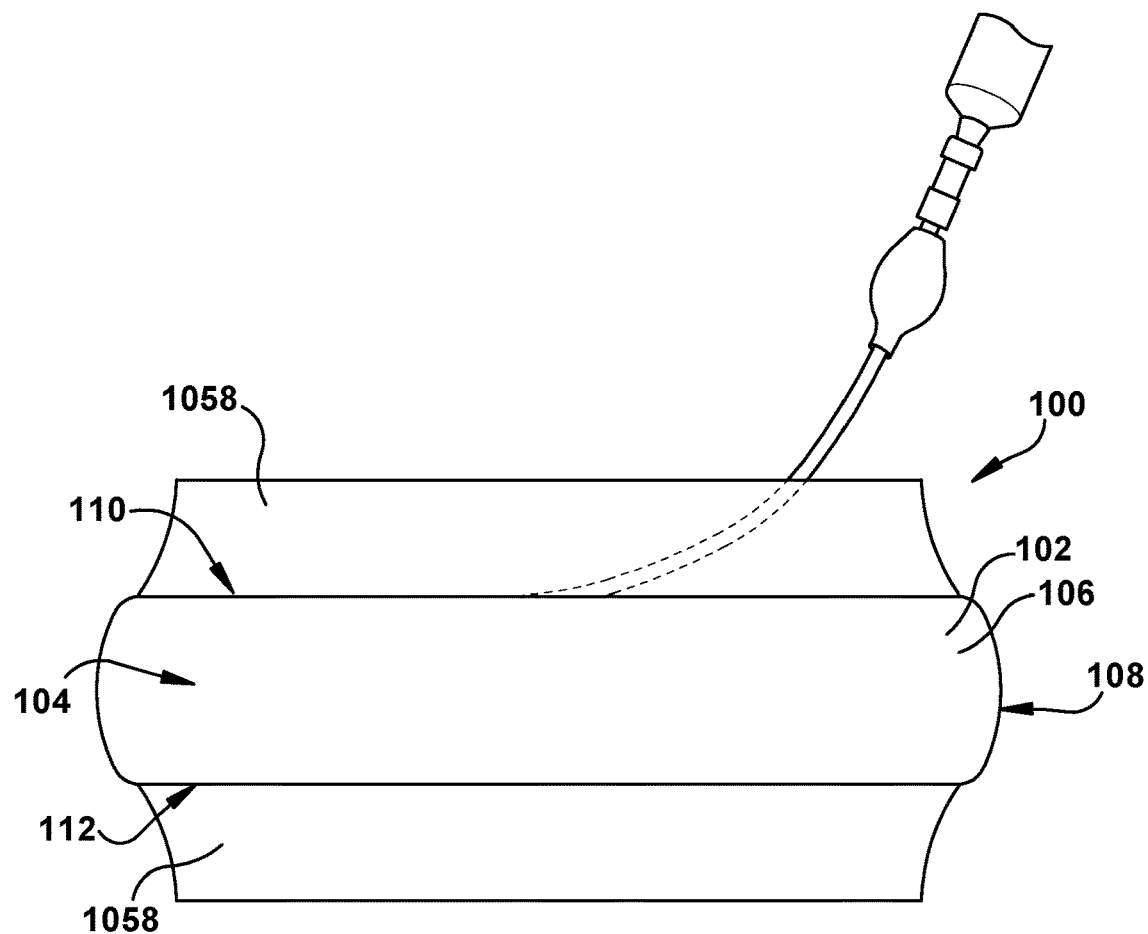
FIG. 10 is a front view of the aspect of FIG. 1.
Figure 11:
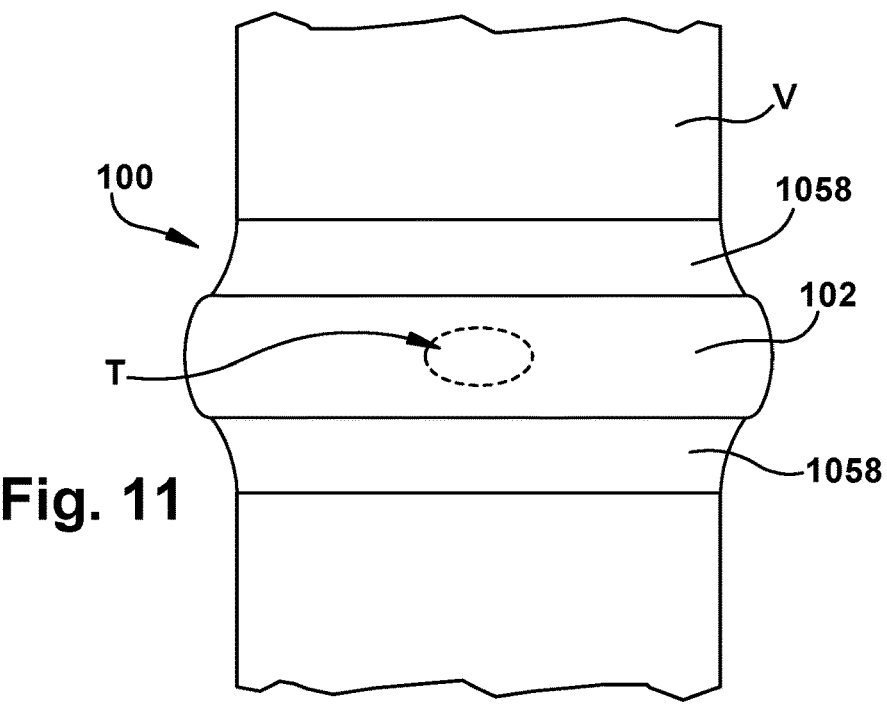
FIG. 11 is a front view of the aspect of FIG. 10 in an example use configuration.

As shown in FIG. 10, at least one of the membrane first and second major edges 110, 112 may have a sealing film 1058 extending laterally therefrom. The sealing film 1058 may be bonded to, integrally formed with, permanently attached to, and/or removably attached to at least one of the membrane first surface 106, the membrane second surface 108, the membrane inflatable space 430, when provided, the membrane first edge 110, the membrane second edge 112, and the plurality of cells 104. The sealing film 1058 may be at least partially formed from an elastomeric material and/or any other appropriate material capable of providing at least a portion of the radially inward pressure R. As shown in FIG. 11, the innate elasticity of the elastomeric material may provide at least a portion of the radially inward pressure R to the portion of the vessel V that is encircled by the sealing film 1058. In particular, the elasticity of the sealing film may cause the sealing film 1058 to compress at least a portion of the vessel V. The sealing film 1058 may substantially seal the target site T at least partially because the sealing film 1058 may at least partially compress at least a portion of the vessel V that is laterally above and/or below the target site T. The sealing film 1058 may at least partially distribute the radially inward pressure R provided by the hemostatic vessel band 100 away from the target site T. The sealing film 1058 is able to at least partially distribute the radially inward pressure R because the surface area of the combined hemostatic vessel band 100 and sealing film 1058 may have less pressure per square unit than what the hemostatic vessel band 100 alone would have.

At least one of the membrane second surface 108 and the plurality of cells 104 may be at least partially formed from, coated, and/or treated with one or more materials, tissues and/or substances that in contact with the blood show tendency to produce a clot (thrombogenic materials). Suitable thrombogenic materials include, but are not limited to, gels, thrombin, and/or any of the enzymes participating in a blood coagulation cascade. The thrombogenic material(s), when present, may assist in hemostasis of the target site T by encouraging clotting of blood. One or more of the cells 104 may be at least partially provided with a surface (either the cell 104 surface itself or a lining) that is made of uneven, textured, non-homogenous, fibrous, and/or porous surface material.

Figure 14:
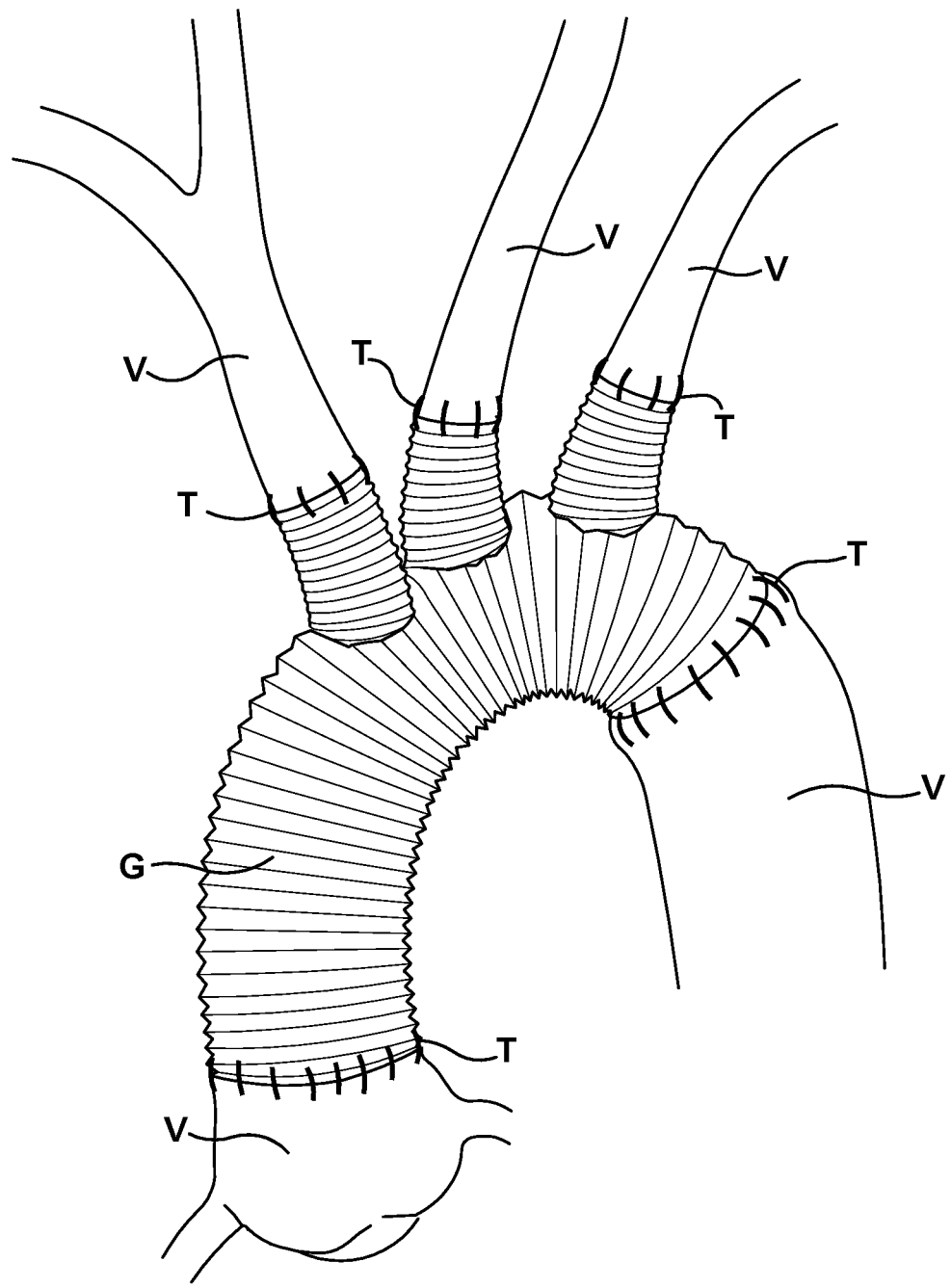

In use, the hemostatic vessel band 100, as described above, is provided to the user. At least one of the membrane second surface 108 and the plurality of cells 104 may be selectively coated with a thrombogenic material. At least one target site T is located on a vessel V. As shown in FIGS. 12-14, the target site T may be at least one anastomosis suture line between two portions of the vessel V (FIG. 12), at least one anastomosis suture line between a portion of the vessel V and a portion of a graft G (FIGS. 13-14), at least one point on the anastomosis suture line, and/or any other appropriate target site T.

Figure 15:
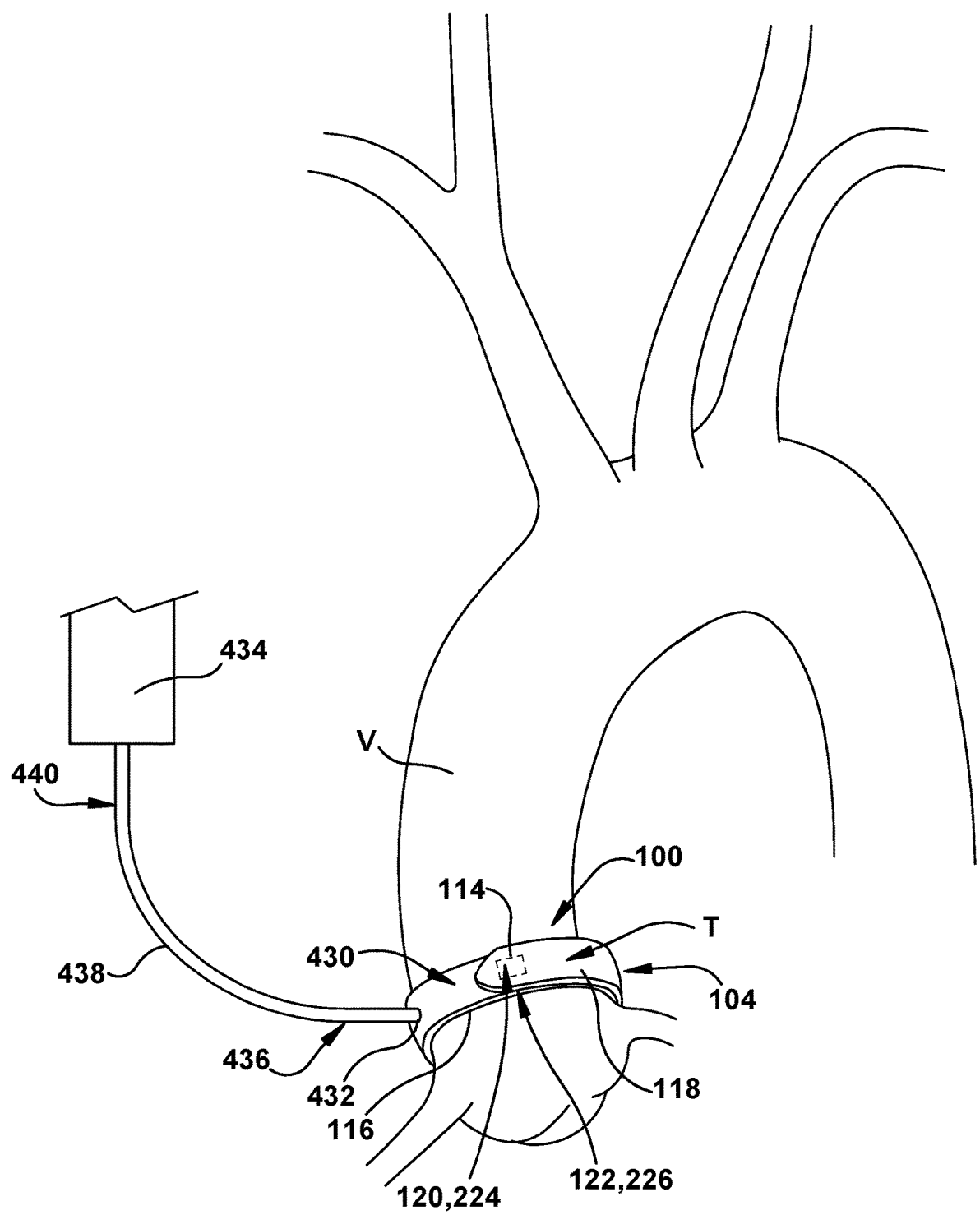
Figure 16:
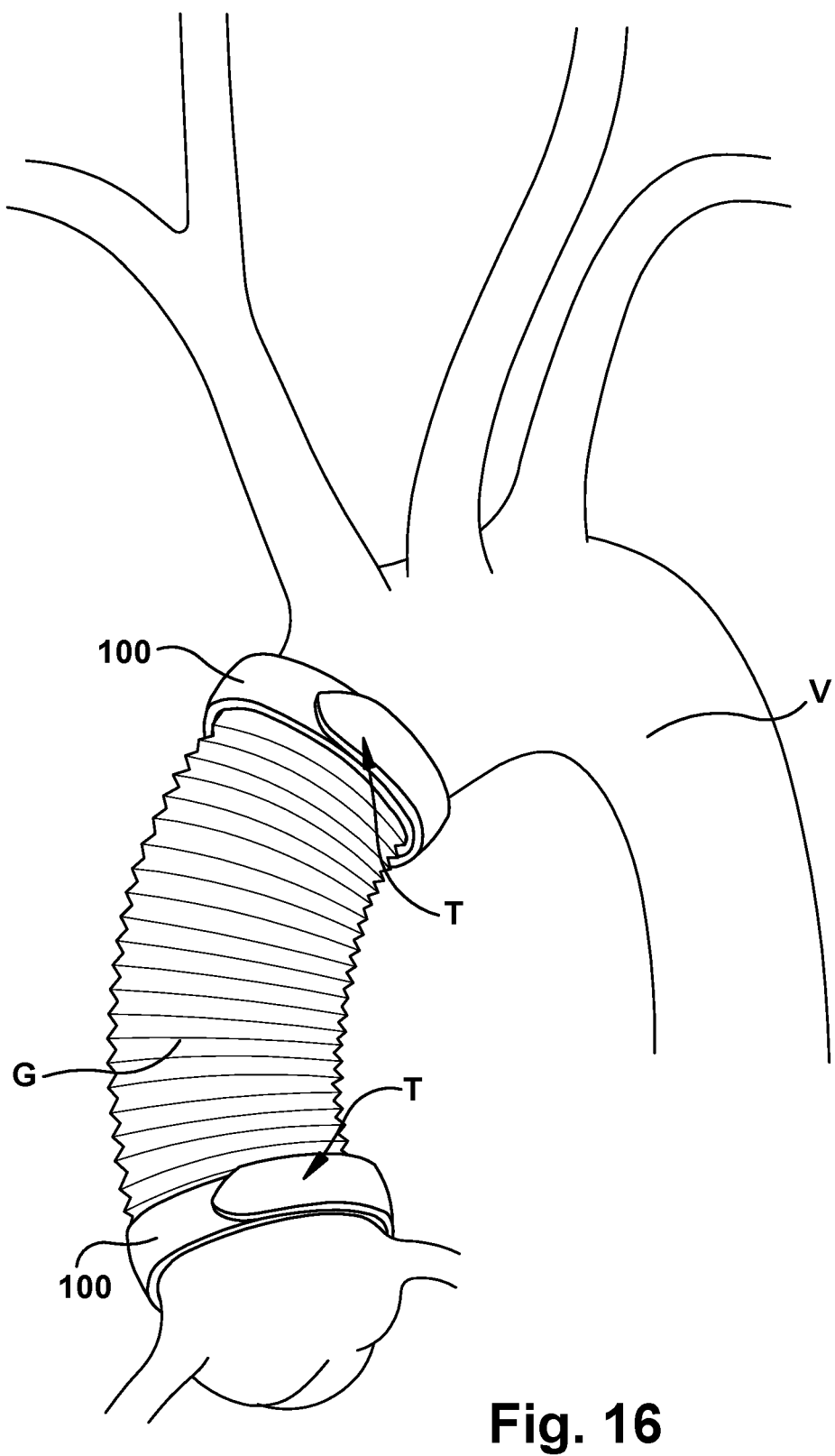
Figure 17:
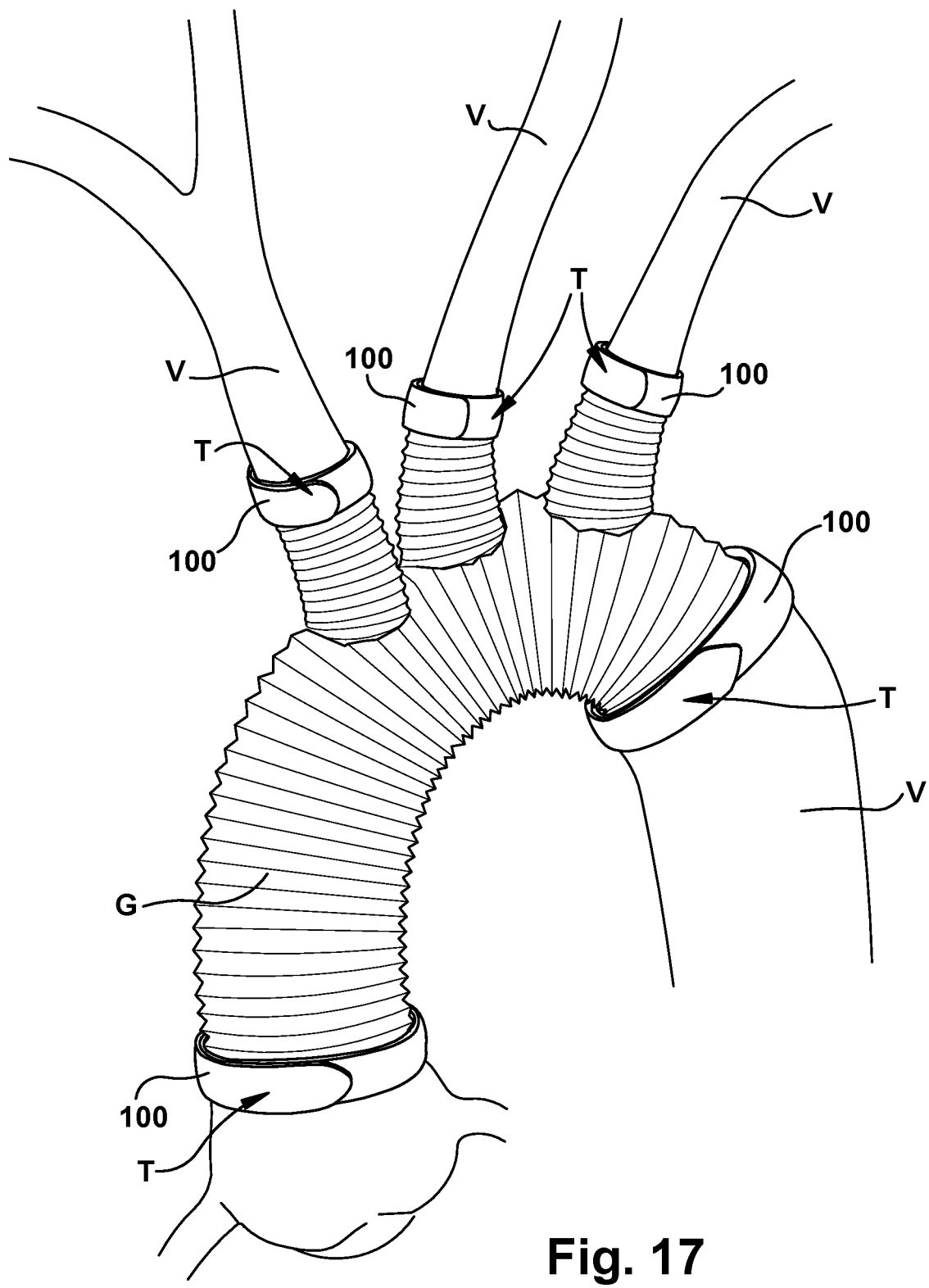

As shown in FIGS. 15-17, the hemostatic vessel band 100 may be directed circumferentially about the vessel V so that at least a portion of the cells 104 are transversely adjacent to at least a portion of the target site T. The at least one first fastening element 120, when provided, may be selectively engaged to the at least one second fastening element 120, when provided, to at least partially encircle and fasten the hemostatic vessel band 100 about the vessel V in a predetermined use position. In particular, as described above, a portion of the membrane first end 114 having the plurality of hooks 224 may be selectively directed to at least partially overlap at least one of the membrane first end 114, the membrane second end 116, and the membrane body 118 so that the plurality hooks 224 may engage the plurality of loops 226. The hemostatic vessel band 100 is placed in the predetermined use position when at least a portion of the vessel V is encircled with the hemostatic vessel band 100 so that at least a portion of the cells 104 is transversely adjacent to at least a portion of the target site T. When the hemostatic vessel band 100 encircles and is fastened to the vessel V, the hemostatic vessel band 100 is in the ringed condition, as described above.

Radially inward pressure R is provided from the hemostatic vessel band 100 to the portion of the vessel V that is encircled by the hemostatic vessel band 100. When the hemostatic vessel band 100 is formed at least partially from the elastomeric material, as described above, the innate elasticity of the elastomeric material may provide at least a portion of the radially inward pressure R to the portion of the vessel V that is encircled by the hemostatic vessel band 100.

As described above, at least a portion of the radially inward pressure R may be provided by the engagement of the first fastening element 120, when provided, to the second fastening element 122, when provided. The amount of radially inward pressure R provided by the engagement of the first and second fastening elements 120, 122 may be selectively adjusted to provide a predetermined amount of radially inward pressure R by placing the first and second fastening elements 120, 122 in a selected fastening condition. In particular, the portion of the membrane first end 114 having the plurality of hooks 224 may be selectively directed from one fastening condition with the plurality of loops 226 to another fastening condition with the plurality of loops 226 in order to adjust the diameter of the ringed hemostatic vessel band 100. In other words, the portion of the membrane first end 114 having the plurality of hooks 224 may be selectively directed from one engagement position with the plurality of loops 226 to another engagement position with the plurality of loops 226 so that the plurality of hooks 224 moves from one position on at least one of the membrane first end 114, the membrane second end 116, and the membrane body 118 to another position on at least one of the membrane first end 114, the membrane second end 116, and the membrane body 118. The resulting increase or decrease in the diameter of the ringed hemostatic vessel band 100 may directly correspondingly increase or decrease the amount of radially inward pressure R that is provided by the hemostatic vessel band 100.

It is contemplated that the hemostatic vessel band 100 may have any desired degree of flexibility in use. For example, once placed into the ring configuration, the hemostatic vessel band 100 may demonstrate adjustment to the vessel size after placement. As another example, if a less-flexible hemostatic vessel band 100 instead achieves desired fixation through being slightly undersized with respect to the vessel size, the hemostatic vessel band 100 might not stretch. If a vessel V shrinks within an already-installed hemostatic vessel band 100, it is possible that a relatively non-flexible hemostatic vessel band 100 may not be configured to adjust to sizes outside its functional "range", which could be desired in particular use environments.

When the hemostatic vessel band 100 includes the inflation valve 432 and the membrane inflatable space 430, as described above, the inflation valve 432 may be selectively connected to the pressure source 434. The membrane inflatable space 430 may be selectively inflated by actuating the pressure source 434 to direct inflation fluid from the pressure source 434, through a least a portion of the inflation valve 432, and into the membrane inflatable space 430. When the pressure line 438 is provided, the inflation valve 432 may be selectively connected to the pressure line distal end 438, and the pressure line proximal end 440 may be selectively connected to the pressure source 434. In such case, the inflation fluid is directed from the pressure source 434, through at least a portion of the pressure line 438, through at least a portion of the inflation valve 432, and into the membrane inflatable space 430. As described above, the inflation of the membrane inflatable space 430 may provide a predetermined portion of the radially inward pressure R to the portion of the vessel V that is encircled by the hemostatic vessel band 100. The amount of inflation fluid directed into the membrane inflatable space 430 may correspond directly to the amount of radially inward pressure R that is provided to the portion of the vessel V that is encircled by the hemostatic vessel band 100. A measurable change of the radially inward pressure R may result in an intended change in size of the hemostatic vessel band 100. It is contemplated that the hemostatic vessel band 100 could be configured to relate a provisional or removal of a particular inflation fluid amount to a predetermined increase or decrease in radially inward pressure and/or a dimension of the hemostatic vessel band. For example, injection of an additional 1 cc of fluid could result in a diameter reduction of the inner band surface of 1 mm, in some use configurations.

Figure 18:
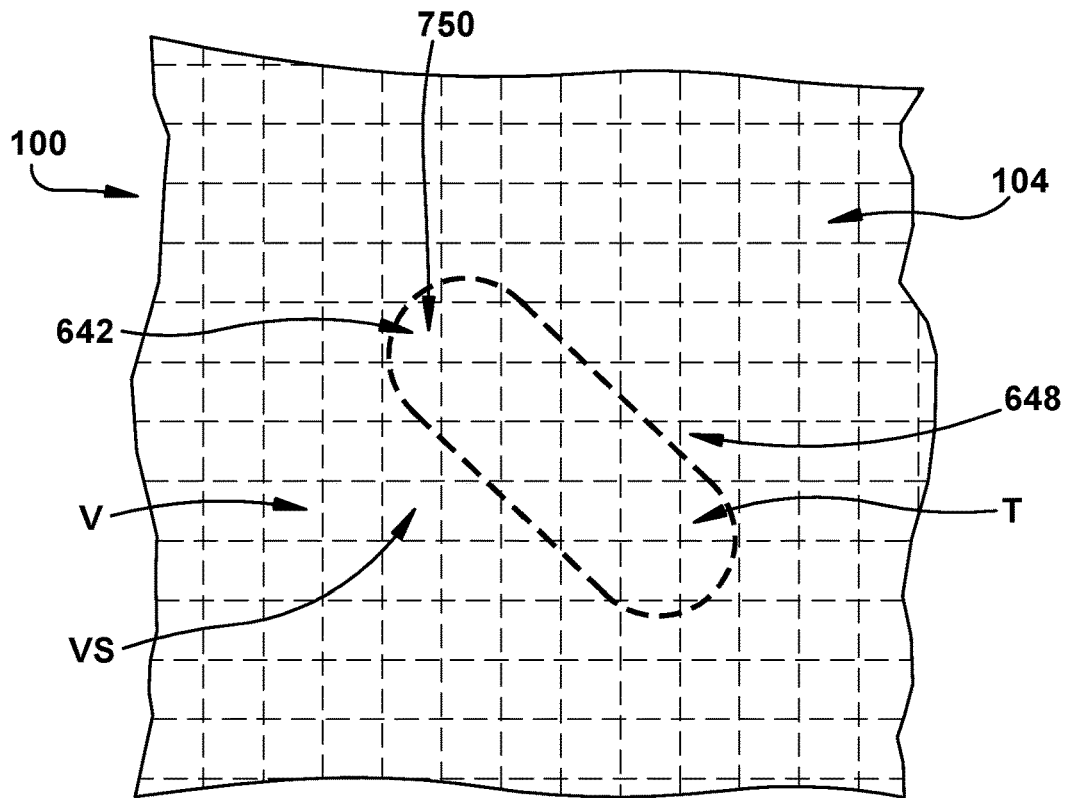
Figure 19:
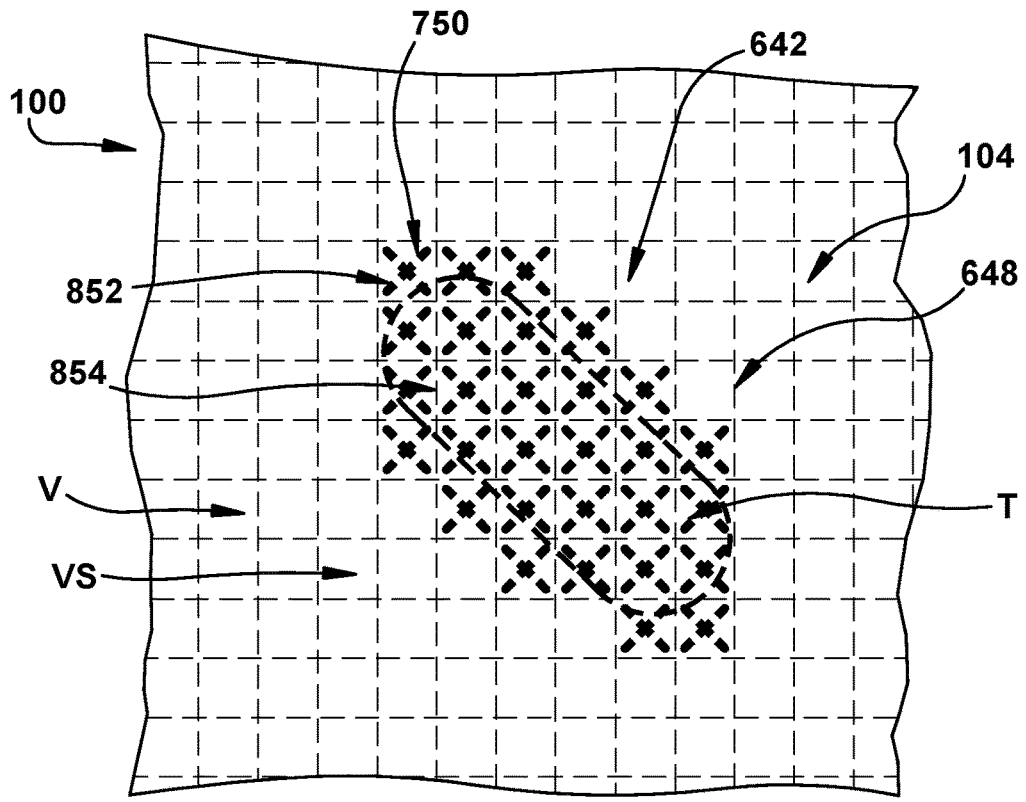

As shown in FIGS. 18-19, with the radially inward pressure R, the portion of the cells 104 which are transversely adjacent to at least a portion of the target site T is caused to engage the target site T. Isolation zones 750 are formed with each cell chamber 642 that is positioned transversely adjacent to at least a portion of the target site T. At least one of the isolation zones 750 has a corresponding bleeding locale 850 at the target site T. Each isolation zone 750 is at least partially isolated 750 from each of the other isolation zones 750 and from any vessel surface VS adjacent to the isolation zone 750. The bleeding locale 850 at the corresponding isolation zone 750 is isolated from at least one of another bleeding locale 850, another isolation zone 750, and a vessel surface VS surrounding the isolation zone 750 so that blood from the bleeding locale 850 is directed into the corresponding isolation zone 750 and is substantially prevented from flowing to at least one of another bleeding locale 850, another isolation zone 750, and the vessel surface VS surrounding the isolation zone 750.

Figure 20:
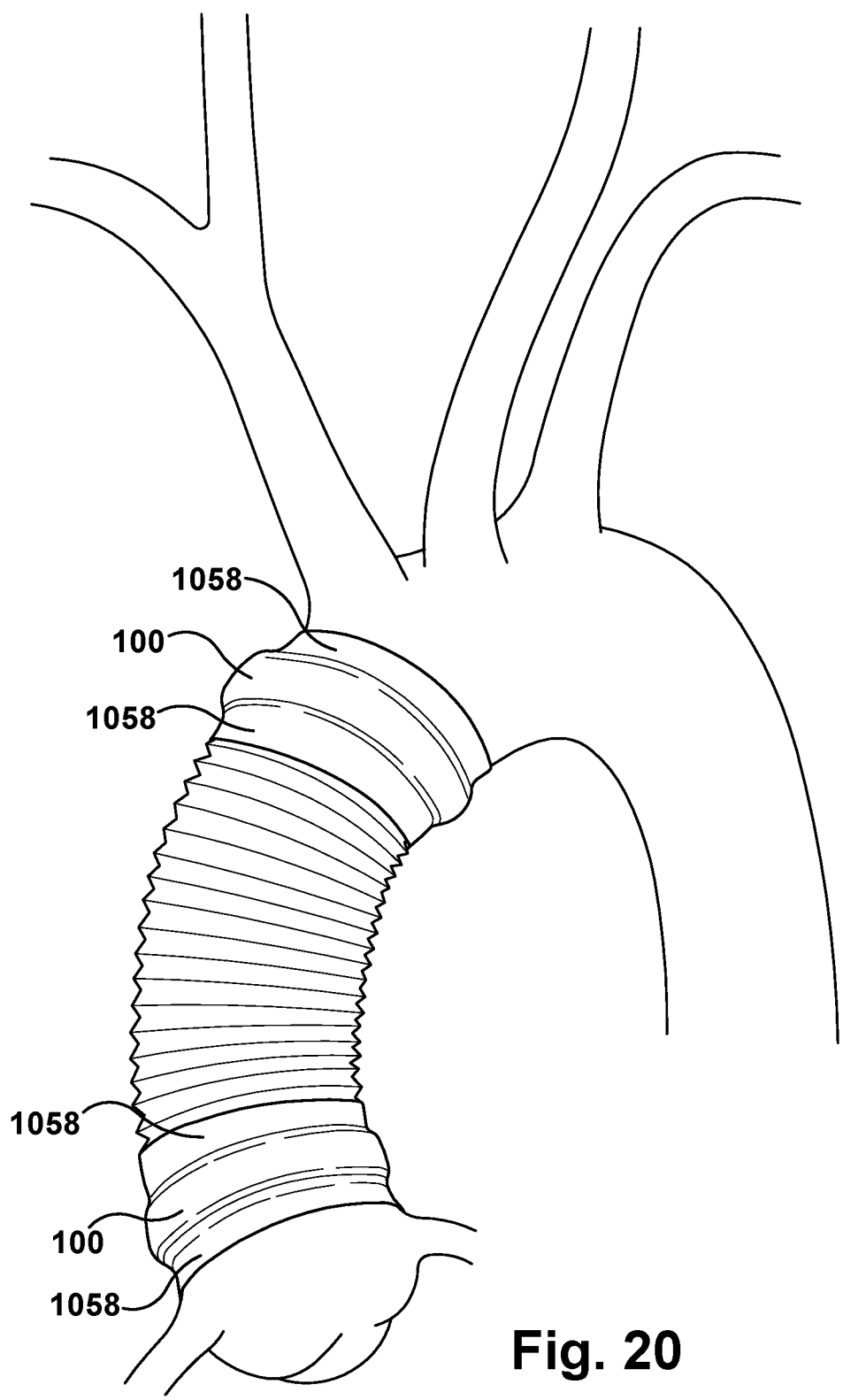
FIG. 20 illustrates the aspect of FIG. 10 in an example use environment.

The hemostatic vessel band 100 may be prevented from egressing from the predetermined use position. The vessel engaging edge 648 maintains contact with the hemostatic vessel band 100 and at least one of the vessel surface VS and the target site T to prevent the hemostatic vessel band 100 from egressing from the predetermine use position. As shown in FIG. 20, the sealing film 1058, when provided, may at least partially seal the target site T and may partially distribute the radially inward pressure R away from the target site R, as described above. As described above, the thrombogenic material, when provided, may at least partially contribute to hemostasis once the hemostatic vessel band 100 encircles the vessel V.

The hemostatic vessel band 100 may be at least partially formed from silicone, polyethylene, polypropylene, any other biocompatible material, or any combination thereof. The hemostatic vessel band 100 may be a continuous band having no separate portions. Alternatively, the hemostatic vessel band 100 may be formed from separate portions that are combined prior to use. The hemostatic vessel band 100 may have a transverse height of about two hundredths (0.25) of a millimeter to about three (3) millimeters. The hemostatic vessel band 100 may have any desired transverse height.

The hemostatic vessel band 100 may assist the user in securing hemostasis of the target site. The hemostasis may be at least partially obtained by the seal 854 for each isolation zone 750 containing the blood and/or other biological material from a corresponding bleeding locale 850 to the corresponding isolation zone 750 in order to at least partially limit the flow of blood and/or other biological material. The hemostasis may be at least partially obtained by the radial pressure R provided by the hemostatic vessel band 100 slowing the flow of blood and/or other biological material.

For example, the hemostatic vessel band 100 could promote hemostasis via at least one of the following mechanisms:
 the pressure of the bleeding may be distributed differently across the surface with preformed cells 104 (the cells 104 provide distribution of those pressure forces, go deep into tissue to isolate one area from another);
 blood movement from the bleeding site may be blocked, and bleeding speed is slower; and/or
 the blood stagnation caused in each cell 104 may provide a certain blood buildup within cells, and once the cells are full with blood, the sealing may even be improved since there is no more space within the cells 104 for blood.

The fixation of the hemostatic vessel band 100 in the ring configuration could become more effective (also through adhesion or molding of blood into the cells 104) to secure the bleeding site as desired, in certain use configurations.

It is contemplated that the hemostatic vessel band 100 may have a plurality of layers. Each layer may have the same or different mechanical features, biologically active materials, drugs, bioabsorbable materials, biodegradable materials, vessel fixation features, any other suitable features and/or materials, or any combination thereof, from any other layer. It is contemplated that the hemostatic vessel band 100 may be temporarily or permanently fastened to at least a portion of the vessel V and at least a portion of the target site T.

It is contemplated that the hemostatic vessel band 100 may be at least partially formed from a shape memory material. The shape memory hemostatic vessel band 100 is configured to be preset in the ringed condition above a transition temperature range. The shape memory hemostatic vessel band 100 is able to be deformed into a second condition from the ringed condition when the hemostatic vessel band 100 is cooled to a temperature below a transition temperature range. The transition temperature range is dependent on the particular ratio of metals and/or materials in the shape memory material. Below the transition temperature range, the shape memory material is highly ductile and may be plastically deformed into a desired shape, such as the second condition. Upon reheating above the transition temperature range, the shape memory material returns to its preset shape, such as the ringed condition. In other words, the shape memory hemostatic vessel band 100 is configured to automatically return to the ringed condition when the hemostatic vessel band 100 is at a temperature above the transition temperature range. The shape memory material may be at a temperature above its transition temperature range when the temperature of the shape memory material is equal to, and/or greater than the temperature of a normal patient body. After the shape memory hemostatic vessel band 100 is directed circumferentially about the vessel V and moved from the second condition to the ringed condition, the shape memory hemostatic vessel band 100 in the ringed condition is fastened circumferentially about the vessel V.

It is contemplated that the hemostatic vessel band 100 is at least partially formed from a bioactive material. Suitable bioactive materials include any material with properties that promote adhesion, tissue buildup (that in its turn may change the band size), absorption of tissue or materials used, and/or have some hydrophilic properties that may affect band size through increased intake of fluid into at least one component of the band. The innate properties of the bioactive material, when present, may cause the bioactive material hemostatic vessel band 100 to fasten circumferentially about the vessel V when the hemostatic vessel band 100 is placed circumferentially about the vessel V in a similar manner as described above for the shape memory material hemostatic vessel band 100.

It is contemplated that sealing film 1058 may be formed at least partially from a bioactive material having bio-adhesive properties. A bioactive material having bio-adhesive properties may be, for example, a material that changes properties of the band after its placement (such as surface tension or radial pressure, filling, better band coupling/attachment to the surface through "cementing/fixation" itself into the blood clot formed between band and vessel). When the hemostatic vessel band 100 having the bioactive material sealing band 1058 is fastened circumferentially about a vessel V inside a patient body, the temperature and/or other environmental conditions inside the patient body may cause the bio-adhesive properties of the bioactive material sealing film 1058 to at least partially adhere to the vessel surface VS.

Though the hemostatic vessel band 100 is shown in the Figures as encircling the vessel surface VS at substantially a perpendicular orientation, it is contemplated that the hemostatic vessel band 100 could instead be placed in an angular relationship to the vessel surface VS, and one of ordinary skill in the art can provide a suitably configured hemostatic vessel band 100 for angular (e.g., "oblique") usage.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A hemostatic vessel band, comprising:
a membrane having a membrane first surface and an oppositely facing membrane second surface, the membrane having a membrane first end, a membrane second end, and a membrane body longitudinally extending an entire distance between the membrane first and second ends to cooperatively define the membrane first and second surfaces, the membrane first end having at least one first fastening element, the membrane second end having at least one second fastening element, the at least one first fastening element being configured to at least partially engage the at least one second fastening element to selectively fasten the hemostatic vessel band circumferentially about a vessel; and
a plurality of cells extending transversely from the membrane second surface, each of the cells being directly adjacent to at least one of the other cells, and the plurality of cells being collectively evenly distributed across an entirety of the membrane second surface,
each of the cells having a cell chamber that is defined by the membrane second surface and a plurality of cell walls, the plurality of cell walls having a vessel engaging edge configured to concurrently contact at least a portion of a vessel surface and at least a portion of a target site on the vessel;
wherein when the hemostatic vessel band is selectively fastened circumferentially about a vessel to at least partially cover the target site, the hemostatic vessel band is configured to apply radially inward pressure to at least a portion of the vessel and at least a portion of the target site, and each cell chamber that is positioned transversely adjacent to at least a portion of the target site forms one isolation zone of a plurality of isolation zones, each isolation zone being at least partially isolated from each of the other isolation zones and from any vessel surface adjacent to the isolation zone.

2. The hemostatic vessel band of claim 1, being formed at least partially from an elastomeric material, the innate elasticity of the elastomeric material providing the radially inward pressure to at least a portion of the vessel and at least a portion of the target site.

3. The hemostatic vessel band of claim 1, including an inflation valve in the membrane, and a membrane inflatable space transversely between the membrane first and second surfaces, the inflation valve selectively placing the inflatable membrane space in fluid communication with a pressure source, the membrane inflatable space being selectively inflated and configured to provide a predetermined radially inward pressure to at least a portion of the vessel and at least a portion of the target site.

4. The hemostatic vessel band of claim 1, wherein the hemostatic vessel encircling band is a continuous band.

5. The hemostatic vessel band of claim 1, wherein at least one of the membrane second surface and the cells is formed from an active thrombogenic material.

6. The hemostatic vessel band of claim 1, wherein at least one of the membrane second surface and the cells is at least partially coated with an active thrombogenic material.

7. The hemostatic vessel band of claim 1, wherein the membrane has membrane first and second major edges, the membrane first major edge being laterally spaced, and oppositely facing, from the membrane second major edge, at least one of the membrane first and second major edges having a sealing film laterally extending therefrom.

8. The hemostatic vessel band of claim 1, wherein each of the cell walls has a first cell edge and the vessel engaging edge, the first cell edge being transversely spaced, and oppositely facing, from the vessel engaging edge, the first cell edge contacting the membrane second surface, the vessel engaging edge being configured to maintain contact between the hemostatic vessel band and at least one of the vessel surface and the target site to prevent the hemostatic vessel band from egressing from a predetermined use position.

9. The hemostatic vessel band of claim 1, wherein at least one of the isolation zones is configured to have a corresponding bleeding locale at the target site, the bleeding locale at the corresponding isolation zone is configured to be isolated from at least one of another bleeding locale, another isolation zone, and a vessel surface surrounding the isolation zone so that blood from the bleeding locale is configured to be directed into the corresponding isolation zone and is configured to be substantially contained within the isolation zone for stagnation therein and accordingly prevented from flowing to at least one of another bleeding locale, another isolation zone, and the vessel surface surrounding the isolation zone.

10. The hemostatic vessel band of claim 1, wherein the first fastening element includes a plurality of hooks extending transversely and directly from the membrane second surface, and the second fastening element includes a plurality of loops, the plurality of loops forming a mesh that transversely extends directly from at least a portion of the membrane first surface.

11. The hemostatic vessel band of claim 1, wherein the hemostatic vessel band has a durometer hardness of 50 Shore A.

12. The hemostatic vessel band of claim 1, wherein each of the cells has a longitudinal width of two (2) millimeters, a lateral length of two (2) millimeters, and a transverse height of about twenty-five hundredths (0.25) to about seventy-five hundredths (0.75) of a millimeter.

13. The hemostatic vessel band of claim 1, wherein the target site on the vessel is at least one anastomosis suture line configured to completely encircle the vessel.

14. The hemostatic vessel band of claim 1, wherein the cells are collectively evenly distributed across an entirety of the membrane second surface.

15. The hemostatic vessel band of claim 1, wherein the hemostatic vessel band is configured to directly contact an entire circumference of the vessel to exert an inwardly compressive force thereupon.

16. A method for assisting in the hemostasis of a vessel, the method comprising:
providing a hemostatic vessel band including a membrane having a membrane first surface and an oppositely facing membrane second surface,
the membrane having a membrane first end, a membrane second end, and a membrane body longitudinally extending an entire distance between the membrane first and second ends to cooperatively define the membrane first and second surfaces, the membrane first end having at least one first fastening element, the membrane second end having at least one second fastening element, and
a plurality of cells extending transversely from the membrane second surface, each of the cells having a cell chamber that is defined by the membrane second surface and a plurality of cell walls, the plurality of cell walls having a vessel engaging edge for concurrently contacting at least a portion of a vessel surface and at least a portion of a target site on the vessel, each of the cells being directly adjacent to at least one of the other cells, and the plurality of cells being collectively evenly distributed across an entirety of the membrane second surface;
locating at least one target site extending entirely around the vessel;
encircling an entire circumference of the vessel with the hemostatic vessel band so that at least a portion of the cells are transversely adjacent to at least a portion of the target site, the hemostatic vessel band directly contacting an entirety of the circumference of the vessel;
selectively engaging the at least one first fastening element to the at least one second fastening element with the first and second fastening elements overlapping one another along at least a portion of the circumference of the vessel to at least partially encircle and fasten the hemostatic vessel band about the vessel;
allowing the portion of the cells which are transversely adjacent to at least a portion of the target site to fill with blood at the target site; and
forming isolation zones with each cell chamber that is positioned transversely adjacent to at least a portion of the target site, each isolation zone being at least partially isolated from each of the other isolation zones and from any vessel surface adjacent to the isolation zone.

17. The method of claim 16, wherein the hemostatic vessel band is formed at least partially from an elastomeric material, the innate elasticity of the elastomeric material providing a radially inward pressure evenly to the circumference of the vessel that is encircled by the hemostatic vessel band.

18. The method of claim 16, wherein the hemostatic vessel band has a inflation valve in the membrane and a membrane inflatable space between the membrane first and second surfaces, the inflation valve selectively placing the membrane inflatable space in fluid communication with a pressure source, the method further including:
  selectively connecting the pressure source to the inflation valve; and
  selectively inflating the membrane inflatable space by actuating the pressure source to direct inflation fluid from the pressure source, through a least a portion of the inflation valve, and into the membrane inflatable space, the inflation of the membrane inflatable space providing a predetermined radially inward pressure to the portion of the vessel that is encircled by the hemostatic vessel band.

19. The method of claim 18, wherein the amount of inflation fluid directed into the membrane inflatable space corresponds directly to the amount of radially inward pressure that is provided to the portion of the vessel that is encircled by the hemostatic vessel band.

20. The method of claim 16, wherein at least one of the membrane second surface and the cells is formed from a thrombogenic material, the thrombogenic material at least partially contributing to hemostasis.

21. The method of claim 16, including prior to encircling at least a portion of the vessel with the hemostatic vessel band, selectively coating at least one of the membrane second surface and the cells with a thrombogenic material, the thrombogenic material at least partially contributing to hemostasis once the hemostatic vessel band encircles the vessel.

22. The method of claim 16, wherein the membrane has membrane first and second major edges, the membrane first major edge being laterally spaced, and oppositely facing, from the membrane second major edge, at least one of the membrane first and second major edges having a sealing film laterally extending therefrom, the sealing film assisting in at least partially sealing the target site, the sealing film at least partially distributing the radially inward pressure away from the target site.

23. The method of claim 16, including preventing the hemostatic vessel band from egressing from a predetermined use position, the vessel engaging edge maintaining contact with the hemostatic vessel band and at least one of the vessel surface and the target site to prevent the hemostatic vessel band from egressing from the predetermined use position.

24. The method of claim 16, wherein at least one of the isolation zones has a corresponding bleeding locale at the target site, the bleeding locale at the corresponding isolation zone being isolated from at least one of another bleeding locale, another isolation zone, and a vessel surface surrounding the isolation zone so that blood from the bleeding point is directed into the corresponding isolation zone and is substantially prevented from flowing to at least one of another bleeding locale, another isolation zone, and the vessel surface surrounding the isolation zone.

25. The method of claim 15, wherein the first fastening element is a plurality of hooks extending transversely and directly from the membrane second surface, and the second fastening element is a plurality of loops, the plurality of loops forming a mesh that transversely extends directly from at least a portion of the membrane first surface.

26. The method of claim 16, wherein
  locating at least one target site on the vessel includes locating at least one anastomosis suture line completely encircling the vessel; and wherein
  encircling an entire circumference of the vessel with the hemostatic vessel band includes overlaying and directly contacting the anastomosis suture line with the hemostatic vessel band about a circumference of the vessel.

27. The method of claim 16, wherein the cells are collectively evenly distributed across an entirety of the membrane second surface.

28. The method of claim 16, wherein encircling an entire circumference of the vessel with the hemostatic vessel band includes directly contacting an entire circumference of the vessel with the hemostatic vessel band to exert an inwardly compressive force thereupon.

* * * * *